United States Patent
Dartnell et al.

(10) Patent No.: US 12,163,915 B2
(45) Date of Patent: Dec. 10, 2024

(54) SEMICONDUCTOR GAS SENSOR AND METHOD FOR SENSING TWO OR MORE GASES USING CONTACT RESISTANCE AND SHEET RESISTANCE

(71) Applicant: Sumitomo Chemical Company Limited, Tokyo (JP)

(72) Inventors: Nicholas Dartnell, Eltisley (GB); Simon Goddard, Impington (GB); Christopher Newsome, St. Ives (GB); Daniel Tobjork, Cambridgeshire (GB)

(73) Assignee: Sumitomo Chemical Company Limited, Tokyo (JP)

( * ) Notice: Subject to any disclaimer, the term of this patent is extended or adjusted under 35 U.S.C. 154(b) by 900 days.

(21) Appl. No.: 17/262,338

(22) PCT Filed: Jul. 23, 2019

(86) PCT No.: PCT/GB2019/052056
§ 371 (c)(1),
(2) Date: Jan. 22, 2021

(87) PCT Pub. No.: WO2020/021247
PCT Pub. Date: Jan. 30, 2020

(65) Prior Publication Data
US 2021/0302365 A1    Sep. 30, 2021

(30) Foreign Application Priority Data

Jul. 23, 2018 (GB) .................................. 1811975

(51) Int. Cl.
*G01N 27/414* (2006.01)
*G01N 27/12* (2006.01)
*G01N 33/00* (2006.01)

(52) U.S. Cl.
CPC ....... *G01N 27/4141* (2013.01); *G01N 27/128* (2013.01); *G01N 33/0031* (2013.01)

(58) Field of Classification Search
None
See application file for complete search history.

(56) References Cited

U.S. PATENT DOCUMENTS

2009/0312954 A1    12/2009 Utriainen

FOREIGN PATENT DOCUMENTS

DE    44 24 342 C1    11/1995
EP    2 833 127 A1    2/2015
(Continued)

OTHER PUBLICATIONS

International Search Report and Written Opinion mailed Oct. 16, 2019 in connection with International Application No. PCT/GB2019/052056.

(Continued)

*Primary Examiner* — J. Christopher Ball
(74) *Attorney, Agent, or Firm* — Wolf, Greenfield & Sacks, P.C.

(57) ABSTRACT

A gas sensor system for measuring a plurality of gases in an environment. The gas sensors system comprises multiple gas sensors where each of the gas sensors includes a pair of electrodes separated by a semiconducting material. The gas pairs of electrodes of the gas sensors are separated by different distances in each of the gas sensors. Resistivity of the semiconducting material of the gas sensors changes in the presence of a first gas and a contact resistivity between the electrodes and the semiconducting material of gas sensors changes in the presence of a second gas. From measurements of total resistivity of each of the gas sensors the presence and/or the concentration of both the first and the second gas sensors can be determined.

8 Claims, 7 Drawing Sheets

(56) References Cited

FOREIGN PATENT DOCUMENTS

| EP | 2 833 128 A1 | 2/2015 |
|---|---|---|
| WO | WO 2007/122287 A1 | 11/2007 |
| WO | WO 2011/006677 A1 | 1/2011 |

OTHER PUBLICATIONS

Combined Search and Examination Report dated Jan. 17, 2019 in connection with GB Application No. 1811975.0.

Hoefer et al., Contact and sheet resistance of SnO2 thin films from transmission-line model measurements. Sensors and Actuators B: Chemical. Jan. 1, 1995;26-27:59-63.

Hoefer et al., Thin-film SnO2 sensor arrays controlled by variation of contact potential-a suitable tool for chemometric gas mixture analysis in the TLV range. Sensors and Actuators B: Chemical. Oct. 1, 1997;44:429-33.

SEMICONDUCTOR GAS SENSOR AND METHOD FOR SENSING TWO OR MORE GASES USING CONTACT RESISTANCE AND SHEET RESISTANCE

RELATED APPLICATIONS

This Application is a national stage filing under 35 U.S.C. § 371 of international PCT application no. PCT/GB2019/052056, filed Jul. 23, 2019, which claims priority to United Kingdom patent application no. GB 1811975.0, filed Jul. 23, 2018, each of which is incorporated herein by reference in its entirety.

BACKGROUND

In some embodiments, the present disclosure relates to sensing a plurality of gases in an environment. The sensors used to sense the gases comprise semiconductor gas sensors and by using a plurality of the semiconductor gas sensors presence and/or concentration of the plurality of gases can be determined from the responses of the plurality of gas sensors. In some embodiments, the gases may comprise alkenes.

Bottom gate thin film transistors have been previously used as gas sensors. For example, such use of thin film transistors as gas sensors is described in Feng et al., "Unencapsulated Air-stable Organic Field Effect Transistor by All Solution Processes for Low Power Vapor Sensing" Scientific Reports 6:20671 DOI: 10.1038/srep20671. In bottom gate thin film transistor gas sensors, a semiconductor layer at the top of the transistor is able to interact with the atmosphere and/or a gas sample. The semiconductor layer is configured to undergo an electronic interaction with a gas to be detected. The transistor comprises a gate that is disposed underneath the semiconductor layer and an electrical output from the thin film transistor is proportional to the amount/concentration of the gas.

EP 2833127 discloses a chemical sensor arrangement with at least two two-terminal metal oxide sensors with a different electrode spacing and a processing unit combining measurements of the at least two sensors to eliminate contact effects and determine gas concentrations.

SUMMARY

A summary of aspects of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects and/or a combination of aspects that may not be set forth.

Ethylene produced by plants can accelerate ripening of climacteric fruit, the opening of flowers, and the shedding of plant leaves. 1-methylcyclopropene (1-MCP) is known for use in inhibiting such processes. It is therefore desirable to determine when ethylene is released from harvested fruit or flowers such that the aforementioned processes may be inhibited. However, once 1-MCP has been released into an environment containing ethylene it may be difficult to differentiate 1-MCP from ethylene.

The present inventors have found that a gas sensor system containing sensors having electrodes in electrical connection with a semiconductor can be used to differentiate between different gases by use of sensors in which the spacings between electrodes are different.

In some embodiments there is provided a gas sensor system comprising a plurality of gas sensors. The gas sensor system includes at least one first gas sensor and at least one second gas sensor. Each gas sensor comprises first and second electrodes and a semiconducting region comprising a semiconductor between and in electrical contact with the first and second electrodes. A distance between the first and second electrodes of the first gas sensor is greater than that of the second gas sensor.

In some embodiments, the gas sensor system comprises a measurement unit configured to measure a resistance of each one of the plurality of sensors. In some embodiments, the resistance may be determined from a current flowing between the electrodes and/or a voltage applied across the electrodes In some embodiments, the gas sensor system comprises a processor unit configured to determine: a contact resistance component and a semiconducting region resistance component of the measured resistances; a presence of or a change in the concentration of the first gas in the event of a change in the contact resistance; and a presence of or a change in the concentration of the second gas in the event of a change in the a semiconducting region resistance.

In some embodiments there is provided a method of identifying a presence of, or a change in a concentration of, a first gas or a second gas in an environment.

In some embodiments, the method comprises receiving measured resistances of a plurality of gas sensors in the environment wherein each of the plurality of sensors comprises first and second electrodes and a semiconducting region comprising a semiconductor between and in electrical contact with the first and second electrodes. A contact resistance component and a semiconducting region resistance component of the measured resistances may be determined.

In the event of a change in the contact resistance, it may be determined if a first gas is present and/or if a concentration of the first gas has changed.

In the event of a change in the a semiconducting region resistance, it may be determined if a second gas, different from the first gas, is present and/or if a concentration of the second gas has changed.

In some embodiments, the plurality of gas sensors may comprise at least one first gas sensor and at least one second gas sensor wherein a distance between the first and second electrodes of the first gas sensor is larger than a distance between the first and second electrodes of the second gas sensor.

In some embodiments there is provided a non-transitory computer readable medium storing instructions which, when executed by a data processing apparatus, cause the data processing apparatus to carry out the method of identifying a presence of, or a change in a concentration of, a first gas or a second gas.

In some embodiments there is provided a gas sensor system including at least one first gas sensing thin film transistor and at least one second gas sensing thin film transistor. Each gas sensing thin film transistor comprises a gate electrode; a gate dielectric; source and drain electrodes; and a semiconducting region between and in electrical contact with the source and drain electrodes. A distance between the source and drain electrodes of the first gas sensing thin film transistor is greater than a distance between the source and drain electrodes of the second gas sensing thin film transistor.

In some embodiments of the present disclosure, the contact resistance for the first and the second electrode may be known in the absence of the gases to be sensed by the gas sensors. In some embodiments of the present disclosure, the resistance of the semiconducting material between the first and the second electrode may be known in the absence of the gases to be sensed by the gas sensors. In embodiments, where the gas sensors comprise thin film transistors, the semiconducting resistance may be known, absent the gases to be sensed, for different voltages applied to the transistor gate. In some embodiments of the present disclosure, changes in the resistance of the gas sensors, changes in the contact resistance and/or the semiconductor resistance produced by the presence of the gases may be used to determine a presence of and or a concentration of each of the plurality of gases being sensed. In embodiments of the present disclosure, a first gas affects the contact resistance and a second gas affects semiconductor resistance so the presence and/or concentration of both the first and the second gas can be determined by changes in resistance of multiple gas sensors.

DESCRIPTION OF THE DRAWINGS

The present disclosure is described in conjunction with the appended figures. It is emphasized that, in accordance with the standard practice in the industry, various features are not drawn to scale. In fact, the dimensions of the various features may be arbitrarily increased or reduced for clarity of discussion.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION OF THE INVENTION

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, electromagnetic, or a combination thereof. Additionally, the words "herein," "above," "below," and words of similar import, when used in this application, refer to this application as a whole and not to any particular portions of this application. Where the context permits, words in the Detailed Description using the singular or plural number may also include the plural or singular number respectively. The word "or," in reference to a list of two or more items, covers all of the following interpretations of the word: any of the items in the list, all of the items in the list, and any combination of the items in the list.

The teachings of the technology provided herein can be applied to other systems, not necessarily the system described below. The elements and acts of the various examples described below can be combined to provide further implementations of the technology. Some alternative implementations of the technology may include not only additional elements to those implementations noted below, but also may include fewer elements.

These and other changes can be made to the technology in light of the following detailed description. While the description describes certain examples of the technology, and describes the best mode contemplated, no matter how detailed the description appears, the technology can be practiced in many ways. Details of the system may vary considerably in its specific implementation, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the technology to the specific examples disclosed in the specification, unless the Detailed Description section explicitly defines such terms. Accordingly, the actual scope of the technology encompasses not only the disclosed examples, but also all equivalent ways of practicing or implementing the technology under the claims.

To reduce the number of claims, certain aspects of the technology are presented below in certain claim forms, but the applicant contemplates the various aspects of the technology in any number of claim forms. For example, while some aspect of the technology may be recited as a computer-readable medium claim, other aspects may likewise be embodied as a computer-readable medium claim, or in other forms, such as being embodied in a means-plus-function claim.

In the following description, for the purposes of explanation, numerous specific details are set forth in order to provide a thorough understanding of implementations of the disclosed technology. It will be apparent, however, to one skilled in the art that embodiments of the disclosed technology may be practiced without some of these specific details.

The techniques introduced here can be embodied as special-purpose hardware (e.g., circuitry), as programmable circuitry appropriately programmed with software and/or firmware, or as a combination of special-purpose and programmable circuitry. Hence, embodiments may include a machine-readable medium having stored thereon instructions which may be used to program a computer (or other electronic devices) to perform a process. The machine-readable medium may include, but is not limited to, floppy diskettes, optical disks, compact disc read-only memories (CD-ROMs), magneto-optical disks, ROMs, random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions. The machine-readable medium includes non-transitory medium, where non-transitory excludes propagation signals. For example, a processor can be connected to a non-transitory computer-readable medium that stores instructions for executing instructions by the processor.

A non-transitory computer readable medium may be used to store instructions which, when executed by a data processing apparatus, cause the data processing apparatus to carry out one or more of the steps of the methods of the embodiments herein. For example, a non-transitory computer readable medium may comprise instructions to cause a data processing apparatus to carry out the step of determining the presence and/or a change in the concentration of one or more gases using data from a number of sensors. The algorithm embodied in such instructions may be, for example, a supervised or unsupervised machine learning method. However, any suitable algorithm known to one of skill in the computer arts for the analysis of data may be used. In the field of machine learning, such algorithms include without limitation a machine learning method comprising a simple or complex regression, a classification method, a clustering method, a principal component analysis method, an ensemble method, a neural network, a reinforcement learning method, or a Bayesian network.

Figure 1:
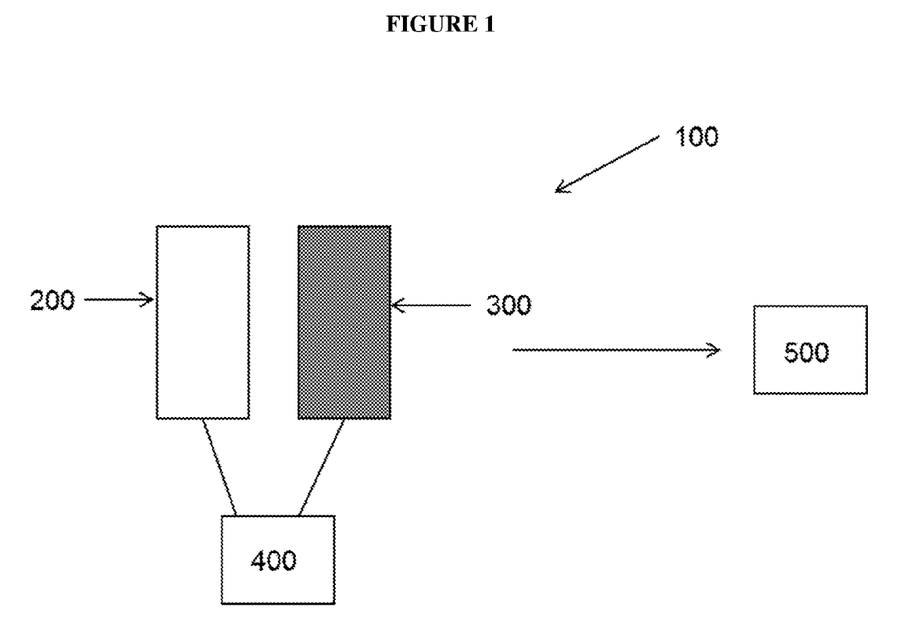
FIG. 1 illustrates a gas sensor system according to some embodiments of the present disclosure.

FIG. 1 is a schematic illustration of a gas sensor system 100 according to some embodiments of the present disclosure. The gas sensor system comprises a first sensor 200 and a second sensor 300. The first and second sensors each comprise first and second electrodes in electrical connection with a semiconducting layer extending between the first and second electrodes.

A separation distance of a semiconducting region between the first and second electrodes of the first sensor is greater than that of the second sensor.

In some embodiments, the sensors 200, 300 are connected to a measurement unit 400 configured to measure the total resistance of each sensor. A total resistance value across the first and second electrodes of each of the first and second sensors changes upon exposure to a first gas or a second gas.

The measurement unit 400 may be in wired or wireless communication with processor unit 500 configured to determine a concentration, and/or a change in concentration, of the first gas or second gas from the measured resistances of each sensor.

FIG. 1 illustrates a gas sensor system having only two different sensors. In other embodiments, the plurality of gas sensors of the gas sensor system may comprise three or more gas sensors with differing electrode separation distances.

FIG. 1 illustrates a gas sensor system having only one first sensor and only one second sensor. In other embodiments, a gas sensor system may comprise a plurality of first sensors and/or a plurality of second sensors, and/or a plurality of any further sensors.

Preferably, the first and second sensors, and (if present) the further sensors differ only in the separation distance of the first and second electrodes. The first, second and any further sensors may be produced simultaneously, the production differing at least, optionally only, in that the first sensor and second sensors are made with different electrode spacings.

Preferably, the plurality of sensors are selected from thin film transistors or chemiresistors. Preferably, the semiconductor is an organic semiconductor.

Organic thin film transistor (OTFT) sensors may be bottom-gate organic thin film transistors (BG-OTFTs) or top gate organic thin film transistors.

Each BG-OTFT may be a bottom contact or top contact device.

Figure 2:
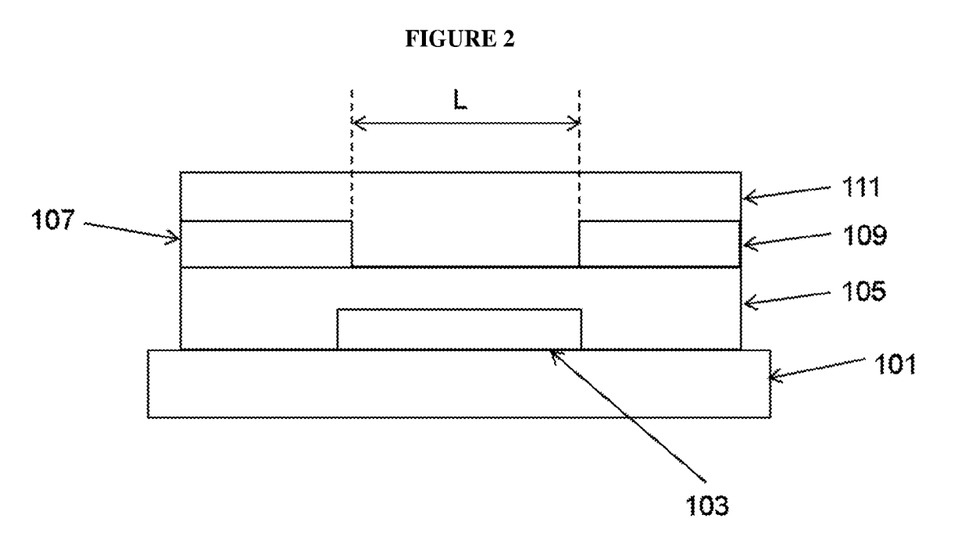
FIG. 2 illustrates a bottom gate, bottom contact organic thin film transistor gas sensor according to some embodiments of the present disclosure.

FIG. 2 is a schematic illustration of a bottom contact BG-OTFT gas sensor in accordance with some embodiments of the present disclosure. The bottom contact BG-OTFT comprises a gate electrode 103 supported on a substrate 101; source electrode 107 and gate electrode 109 defining a channel length L in an organic semiconductor layer 111 extending between the source and drain electrodes; and a dielectric layer 105 between the gate electrode and the source and drain electrodes. The organic semiconductor layer 111 may at least partially or completely cover the source and drain electrodes.

The length of the channel defined between the source and drain electrodes of the first and second source and drain and gate electrodes of the first and second OTFT sensors may be up to 500 microns. Preferably the channel length is less than 200 microns, more preferably less than 100 microns.

A layer "between" and/or "disposed between" two other layers, as described herein, may be in direct contact with each of the two layers or may be between or may be spaced apart from one or both of the two other layers by one or more intervening layers.

As used herein, a material "over" and/or "disposed over" a layer means that the material is in direct contact with the layer or is spaced apart therefrom by one or more intervening layers.

As used herein, a material "on" and/or "disposed on" a layer means that the material is in direct contact with the layer.

In a sensor system comprising a plurality of gas sensors including first, second and optionally further (third, fourth . . . nth) OTFT sensors, the first and second electrodes are the source and drain electrodes and the separation distance between these first and second electrodes is channel length L.

Figure 3:
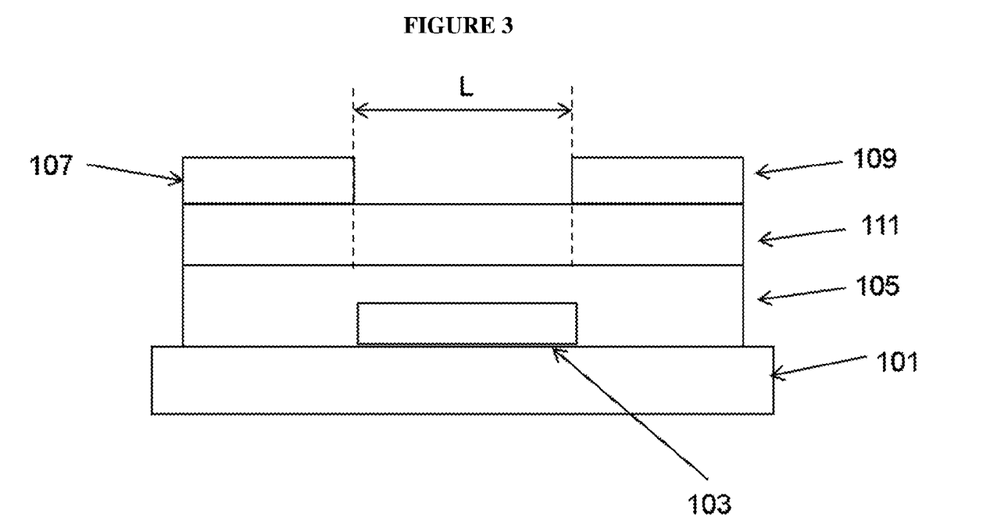
FIG. 3 illustrates a bottom gate, top contact organic thin film transistor gas sensor according to some embodiments of the present disclosure.

FIG. 3 is a schematic illustration of a top-contact BG-OTFT gas sensor according to some embodiments. The top-contact BG-OTFT is as described with reference to FIG.

2 except that the organic semiconductor layer 111 is between the dielectric layer 105 and the source and drain electrodes 107, 109.

Figure 4:
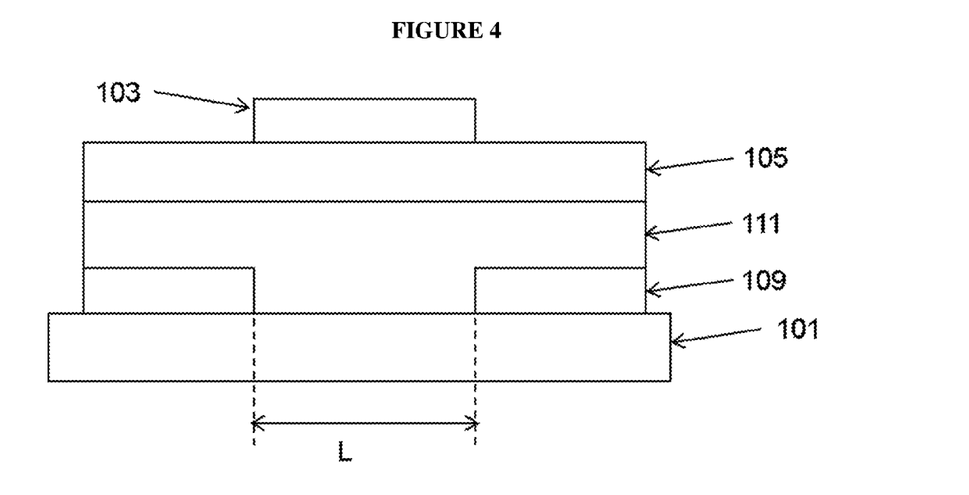
FIG. 4 illustrates a top gate organic thin film transistor gas sensor according to some embodiments of the present disclosure.

FIG. 4 is a schematic illustration of a top gate OTFT gas sensor in accordance with some embodiments of the present disclosure. The top gate OTFT comprises source and drain electrodes 107, 109; an organic semiconductor layer 111; and a dielectric layer 105 between the gate electrode 103 and the organic semiconductor layer. The dielectric layer of the top-gate OTFT is a gas-permeable material, preferably an organic material, which allows permeation of the gas or gases to be sensed through the dielectric layer to the organic semiconducting layer.

First and second OTFT sensors as described herein are preferably BG-OTFT sensors, more preferably bottom contact BG-OTFTs.

Gas sensors described herein may be chemiresistors. Chemiresistors as described herein may be vertical or horizontal chemiresistors.

Figure 5A:
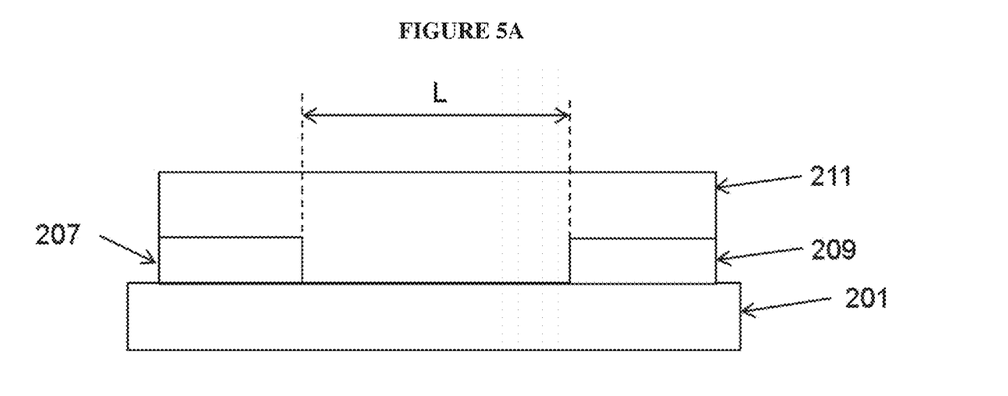
FIG. 5A illustrates a bottom contact horizontal chemiresistor gas sensor according to some embodiments of the present disclosure.

FIG. 5A illustrates a bottom contact horizontal chemiresistor gas sensor. By "bottom contact chemiresistor" as used herein is meant that electrodes of the chemiresistor lie between a substrate and an organic semiconducting layer of the chemiresistor The chemiresistor comprises first and second electrodes 207 and 209 separated by a distance L and an organic semiconductor layer 211 provided between, and in electrical connection with, the first and second electrodes. The first and second electrodes may be interdigitated. The chemiresistor may be supported on any suitable substrate 201, for example a glass or plastic substrate.

Figure 5B:
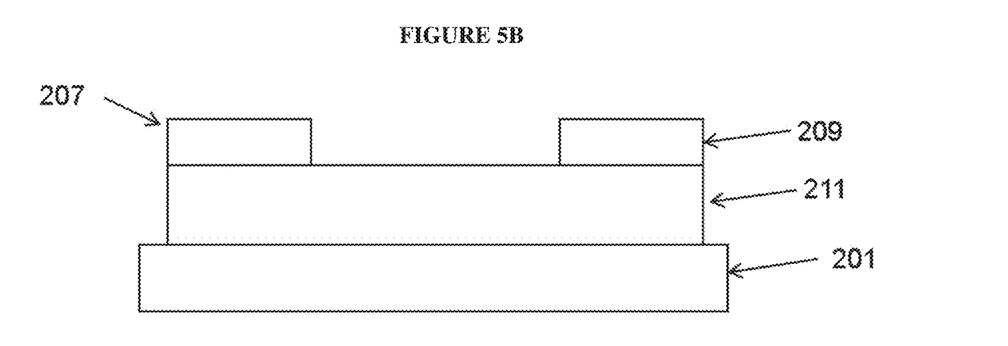
FIG. 5B illustrates a top contact horizontal chemiresistor gas sensor according to some embodiments of the present disclosure.

FIG. 5B illustrates a top contact horizontal chemiresistor gas sensor according to an embodiment. By "top contact chemiresistor" as used herein is meant that an organic semiconducting layer of the chemiresistor lies between electrodes and a substrate of the chemiresistor Integers of the chemiresistor of FIG. 5B are as described with reference to FIG. 5A.

In some embodiments, the first and second electrodes of a horizontal chemiresistor may be separated by a distance of between 5-500 microns, optionally 50-500 microns.

Figure 6:
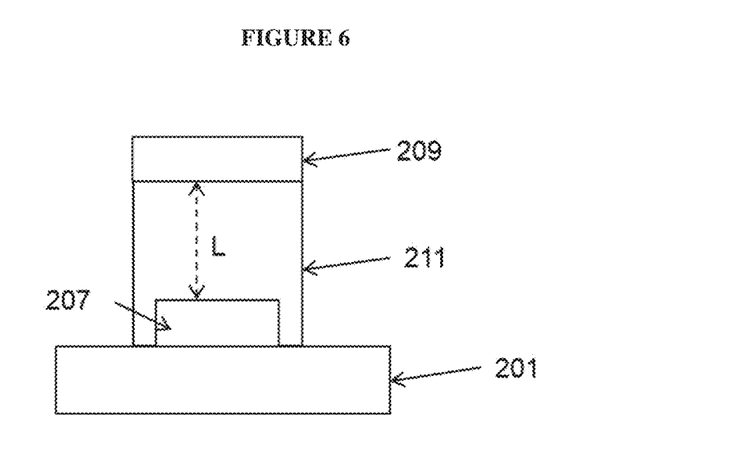
FIG. 6 illustrates a vertical chemiresistor gas sensor according to some embodiments of the present disclosure.

FIG. 6 illustrates a vertical chemiresistor gas sensor according to some embodiments. The chemiresistor comprises a first, bottom electrode 207; a second, top electrode 209 over the first electrode; and an organic semiconductor layer 211 between, and in electrical connection with, the first and second electrodes. The bottom electrode 207 lies between the substrate and both the organic semiconducting layer 211 and the second, top electrode 209.

In some embodiments, the first and second electrodes of a vertical chemiresistor as described herein may be separated by a distance of between 20 nm-10 microns, optionally 50-500 nm.

Gas Sensor Measurements and Gas Identification

The total resistance across the first and second electrodes of a gas sensor as described herein comprises contact resistance, i.e. resistance at each of the first electrode and second electrode interfaces with the semiconducting region, and bulk resistance of the semiconducting region. Resistance of the electrodes themselves may be assumed to be negligible and constant.

The proportion of total sensor resistance attributable to contact resistance may be made higher by one or more of: using a high mobility semiconductor; and having a large electrode work function—semiconductor energy level (ionisation potential or electron affinity) gap.

Certain gases may alter the bulk resistance of a semiconductor of a sensor as described herein, for example ethylene.

Certain gases may alter the contact resistance at the interface of a first and second electrode and a semiconducting region of a sensor as described herein, for example due to a change in the work function at the electrode surface which may be as a result of binding of the gas to the electrode surface, such as a gas having a dipole moment such as 1-MCP.

Schottky current dependence on work function may mean that even a relatively small change in work function $\Delta\phi$ has a large effect on currents $J_1$ and $J_2$ at these work functions:

$$J_2/J_1 = e^{-(\Delta\phi/kT)}$$

Use of a gas sensor system containing sensors with different electrode spacings as described herein may enable differentiation between a first gas which alters total resistance of the device mainly or only by altering contact resistance, and a second gas which alters total resistance of the device mainly or only by altering resistance of the semiconductor in the semiconducting region.

In some embodiments, gas sensors of the gas sensor system are exposed to a gaseous atmosphere and the responses of the sensors are measured.

In some embodiments, the gas sensor system may comprise a gas sensor system for sensing an alkene. In some embodiments, the gas sensor may be configured to sense 1-methylcyclopropene (1-MCP) and/or ethylene. In some embodiments, the gas sensor system as described herein may be used for detecting ethylene and/or 1-MCP in an environment in which one or both of ethylene and 1-MCP may be present. However, as persons of skill in the art will understand, the gas sensor system described herein may be used to measure any gases where the first gas changes a contact resistance of a semiconductor device and a second gas changes a semiconductor resistance of the semiconductor device.

The presence in an environment of a first gas which can alter the contact resistance of a sensor as described herein, such as 1-MCP, may be may be determined by determining a change in the contact resistance of the gas sensors of a gas sensor system as described herein.

A contact resistance component of the total resistance of each gas sensor may be determined by extrapolating the measured total resistances to a first electrode-second electrode distance of 0. If the contact resistance changes upon exposure of the gas sensor system to the environment of interest then it may be determined that the first gas is present. If the contact resistance changes while exposed to the environment of interest then it may be determined that the concentration of the first gas has changed (i.e. increased or decreased).

Contact resistances may be determined in a controlled environment, for example a nitrogen atmosphere, before the gas sensor system is exposed to the environment of interest.

The presence in an environment of a second gas which can be absorbed by the semiconductor of gas sensors as described herein, such as ethylene, may be determined by determining a change in the resistance per unit length of a semiconducting region of the gas sensors. If the concentration of a gas absorbed in the semiconductor changes then the change in total resistance will be larger for gas sensors with a larger first electrode-second electrode distance. This change in resistance per unit length (as distinct from the contact resistance) is apparent from a change in gradient of total resistance vs. first electrode-second electrode distance.

If the resistance per unit length of the semiconducting region changes upon exposure of the gas sensor system to the environment of interest then it may be determined that the second gas is present. If the resistance per unit length of the semiconducting region changes while exposed to the environment of interest then it may be determined that the concentration of the second gas has changed (i.e. increased or decreased).

Resistance per unit length of the semiconducting region in a controlled environment, for example a nitrogen atmosphere, may be determined before the gas sensor system is exposed to the environment of interest.

Preferably, the first gas has little or no effect on resistance per unit length of the semiconducting region of the gas sensors.

Preferably, the second gas has little or no effect or contact resistance of the gas sensors.

A gas sensor system as described herein may be calibrated for first and/or second gases by measuring its response to known concentrations of first and/or second gases such that a concentration of a first gas and/or second gas may be determined when the gas sensor system is in use.

In use, the gas sensor system may be placed in an environment in which first and/or second gases may be present. The total resistance of each of the sensors may be measured periodically and changes in the first and/or second gas concentrations may be determined from changes in the measured resistances.

The gas sensor system may be used in an environmental atmosphere in which alkenes may be present, for example a warehouse in which harvested climateric fruits and/or cut flowers are stored and in which ethylene may be generated.

If ethylene concentration reaches or exceeds a predetermined threshold value, which may be a predetermined value greater than 0, then 1-MCP may be released from a 1-MCP source to retard the effect of the ethylene, such as ripening of fruit or opening of flowers in the environment. The concentration of 1-MCP in such an environment is suitably no more than about 10 ppm or about 5 ppm.

Optionally, 1-MCP may be released into the atmosphere if 1-MCP concentration falls to or below a threshold 1-MCP concentration value as determined by the gas sensor system. The threshold 1-MCP concentration value may be 0 or a predetermined positive value.

1-MCP may be released automatically from a 1-MCP source or an alert or instruction may be generated to manually release 1-MCP from a 1-MCP source in response to signal from the gas sensor system upon determination that 1-MCP concentration is at or below a threshold value and/or in response to a determination that ethylene concentration is at or exceeds a threshold value.

The processor unit of the gas sensor may be in wired or wireless communication with a controller which controls automatic release of 1-MCP from a 1-MCP source and/or a user interface providing information on the presence and/or concentration of ethylene and/or 1-MCP in the environment.

An environment in which an alkene may be present may be divided into a plurality of zones if the concentration of an alkene or alkenes may differ between zones, each zone comprising a gas sensor system according to the present invention and a source of 1-MCP. For example, a warehouse may comprise a plurality of zones.

The gas sensor system may comprise one or more control gas sensors, optionally one or more OTFT or chemiresistor gas sensors, to provide a baseline for measurements of the first and second and any further sensors to take into account variables such as one or more of humidity, temperature, pressure, variation of sensor parameter measurements over time (such as variation of OTFT sensor drain current over time), and gases other than a target gas or target gases in the atmosphere. One or more control gas sensors may be isolated from the atmosphere, for example by encapsulation of the or each control sensor, to provide a baseline measurement other than gases in the atmosphere.

The response of the first and second sensors of the gas sensor system to background gases other than the target gases for detection, for example air or water vapour, may be measured prior to use to allow subtraction of the background from measurements of the gas sensor system when in use.

Each of the sensors of the gas sensor system may be supported on a common substrate and/or contained in a common housing.

In use, each sensor may be connected to a common power source, or two or more of the sensors may be powered by different power sources.

In use, power to all of the sensors of the gas sensor may be controlled by a single switch or power to two or more of the sensors may be controlled by different switches.

Electrodes

The first and second electrodes can be selected from a wide range of conducting materials for example a metal (e.g. gold), metal alloy, metal compound (e.g. indium tin oxide) or conductive polymer.

In the case of an OTFT, the gate electrode may be selected from any conducting material, for example a metal (e.g. aluminium), a metal alloy, a conductive metal compound (e.g. a conductive metal oxide such as indium tin oxide) or a conductive polymer.

Semiconductor Layer

The semiconductor layer of gas sensors described herein may comprise or consist of an organic or inorganic semiconductor.

Organic semiconductors as described herein may be selected from conjugated non-polymeric semiconductors; polymers comprising conjugated groups in a main chain or in a side group thereof; and carbon semiconductors such as graphene and carbon nanotubes.

Exemplary inorganic semiconductors include, without limitation, n-doped silicon; p-doped silicon; compound semiconductors, for example III-V semiconductors such as GaAs or InGaAs; doped or undoped metal oxides; doped or undoped metal sulfides; doped or undoped metal selenides; or doped or undoped metal tellurides. It will be appreciated that an inorganic semiconductor may be used in place of an organic semiconductor as described anywhere herein.

An organic semiconductor layer of the first or second sensors may comprise or consist of a semiconducting polymer and/or a non-polymeric organic semiconductor. The organic semiconductor layer may comprise a blend of a non-polymeric organic semiconductor and a polymer. Exemplary organic semiconductors are disclosed in WO 2016/001095, the contents of which are incorporated herein by reference.

The organic semiconductor layers of the first and second BG-OTFT gas sensors preferably comprise or consist of only one organic semiconductor. The organic semiconductor layer of first and second top-gate organic thin film transistor gas sensors is preferably a mixture of a non-polymeric and polymeric organic semiconductor.

The organic semiconducting layer of a gas sensor may be deposited by any suitable technique, including evaporation and deposition from a solution comprising or consisting of one or more organic semiconducting materials and at least one solvent. Exemplary solvents include benzenes with one or more alkyl substituents, preferably one or more $C_{1-10}$ alkyl substituents, such as toluene and xylene; tetralin; and chloroform. Solution deposition techniques include coating and printing methods, for example spin coating dip-coating, slot-die coating, ink jet printing, gravure printing, flexographic printing and screen printing.

Optionally, the organic semiconducting layer of an organic thin film transistor has a thickness in the range of about 10-200 nm.

Dielectric Layer

The dielectric layer of an OTFT gas sensor as described herein comprises a dielectric material. Preferably, the dielectric constant, k, of the dielectric material is at least 2 or at least 3. The dielectric material may be organic, inorganic or a mixture thereof. Preferred inorganic materials include $SiO_2$, SiNx and spin-on-glass (SOG). Preferred organic materials are polymers and include insulating polymers such as poly vinylalcohol (PVA), polyvinylpyrrolidine (PVP), acrylates such as polymethylmethacrylate (PMMA) and benzocyclobutanes (BCBs), poly(vinyl phenol) (PVPh), poly(vinyl cinnamate) P(VCn), poly(vinylidene fluoride-co-hexafluoropropylene) P(VDF-HFP), P(VDF-TrFE-CTFE), and self-assembled monolayers, e.g. silanes, on oxide. The polymer may be crosslinkable. The insulating layer may be formed from a blend of materials or comprise a multi-layered structure. In the case of a bottom-gate device, the gate electrode may be reacted, for example oxidised, to form a dielectric material.

The dielectric material may be deposited by thermal evaporation, vacuum processing or lamination techniques as are known in the art. Alternatively, the dielectric material may be deposited from solution using, for example, spin coating or ink jet printing techniques and other solution deposition techniques discussed above. In the case of a bottom gate OTFT, the dielectric material should not be dissolved if an organic semiconductor is deposited onto it from solution. In the case of a top-gate OTFT, the organic semiconductor layer should not be dissolved if the dielectric is deposited from solution.

Techniques to avoid such dissolution include: use of orthogonal solvents for example use of a solvent for deposition of the organic semiconducting layer that does not dissolve the dielectric layer in the case of a bottom gate device or vice versa in the case of a top gate device; cross linking of the dielectric layer before deposition of the organic semiconductor layer in the case of a bottom gate device; or deposition from solution of a blend of the dielectric material and the organic semiconductor followed by vertical phase separation as disclosed in, for example, L. Qiu, et al., Adv. Mater. 2008, 20, 1141.

The thickness of the dielectric layer is preferably less than 2 micrometres, more preferably less than 500 nm.

The substrate of a sensor as described herein may be any insulating substrate, optionally glass or plastic.

Use of first and second sensors has been described herein with reference to 1-MCP and ethylene, however it will be appreciated that first and second sensors and gas sensor systems comprising the sensors described herein may be used in detection of strained alkenes generally, optionally compounds comprising a cyclopropene or cyclobutene group, of which alkylpropenes such as 1-MCP are examples; in detection of aliphatic alkenes, optionally ethylene, propene, 1-butene or 2-butene; and/or in detection of compounds with a dipole moment, such as hydrocarbons which do not have a mirror plane bisecting a carbon-carbon bond of the hydrocarbon. Preferably, compounds with a dipole moment as described herein have a dipole moment of greater than 0.2 Debyes optionally greater than 0.3 or 0.4 Debyes.

Examples

Effect of Alkenes on Bulk Semiconductor Resistance

A device of an organic semiconductor between two closely spaced gold electrodes was used to determine the effect of an alkene on bulk semiconductor resistance.

The device was formed by evaporating gold contacts (40 nm thick, spaced ~40 microns apart) onto a layer of Semiconducting Polymer 1 (40 nm).

Semiconducting Polymer 1

Figure 7:
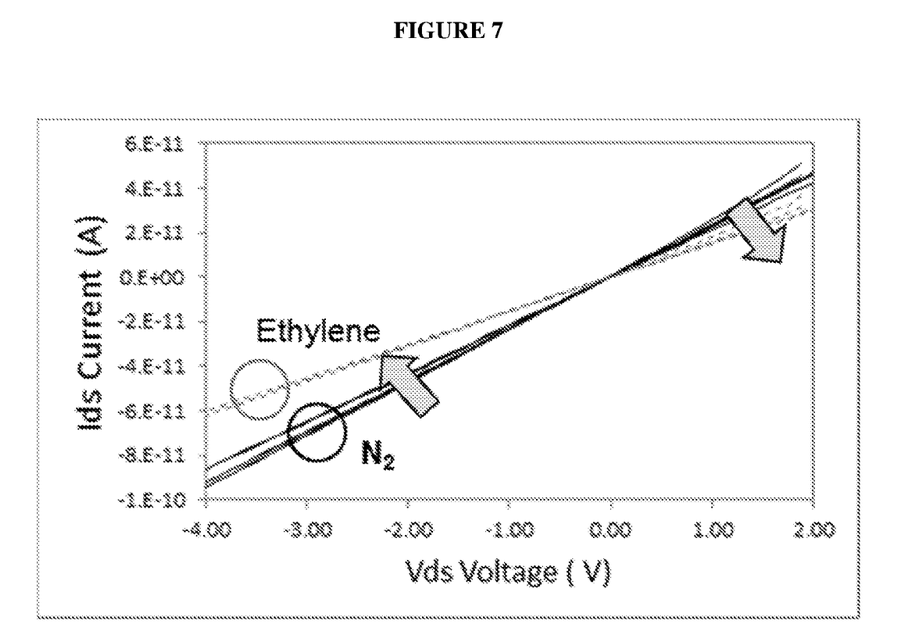
FIG. 7 is a graph of current vs. voltage of an OTFT sensor according to an embodiment in an inert ($N_2$) environment and upon exposure to ethylene.

With reference to FIG. 7, the gradient obtained from an IV sweep across the electrodes after exposure to ethylene (1000 ppm, dashed line) is shallower than that obtained in a nitrogen environment (solid line), indicating an increase in bulk resistance upon exposure to ethylene.

In contrast, the gradient upon exposure to 1-MCP (1000 ppb) was unchanged.

Without wishing to be bound by any theory, it is believed that ethylene is absorbed into the semiconductor more readily than the larger 1-MCP molecule, and as such ethylene has a larger effect on bulk resistance of the semiconductor than 1-MCP.

Effect of Alkenes on Contact Resistance

A series of top-gate OTFTs with a channel length L of 30, 40 and 60 microns between gold source and drain electrodes were exposed to either 1-MCP or ethylene.

To form the OTFTs, a crosslinked dielectric layer was formed by spin-coating and crosslinking an insulating polymer onto an aluminium gate electrode (300 nm) supported on a PEN substrate. A semiconducting layer (40 nm) was formed on the dielectric layer by spin-coating Semiconducting Polymer 1, illustrated above, to a thickness of 40 nm. Gold source and drain electrodes (40 nm) were formed on the semiconducting layer by evaporation.

The effect on contact resistance at the semiconducting region/electrode interface was determined by measuring current as a function of the drain to source voltage at a fixed gate voltage.

Total device resistance increases with increasing spacing. A contact resistance component of the total device resistance was determined by extrapolating the resistance to a spacing of 0.

Figure 8A:
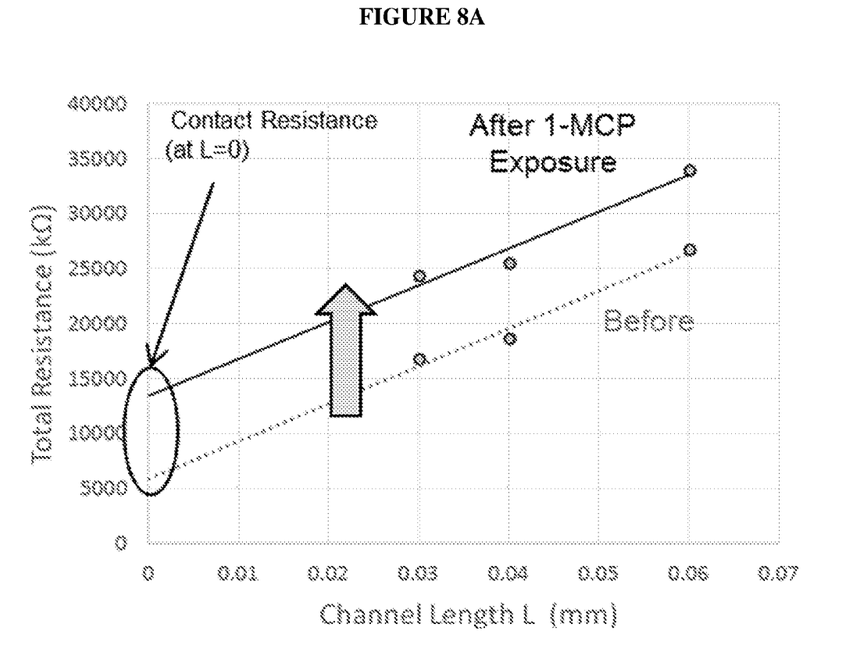
FIG. 8A is a graph of total resistance vs. channel length for a series of OTFT gas sensors having differing channel lengths in an inert (N2) environment and after exposure to 1-MCP.

With reference to FIG. 8A, contact resistance is higher after exposure to 1-MCP (solid line) than contact resistance before exposure to 1-MCP (dashed line).

Figure 8B:
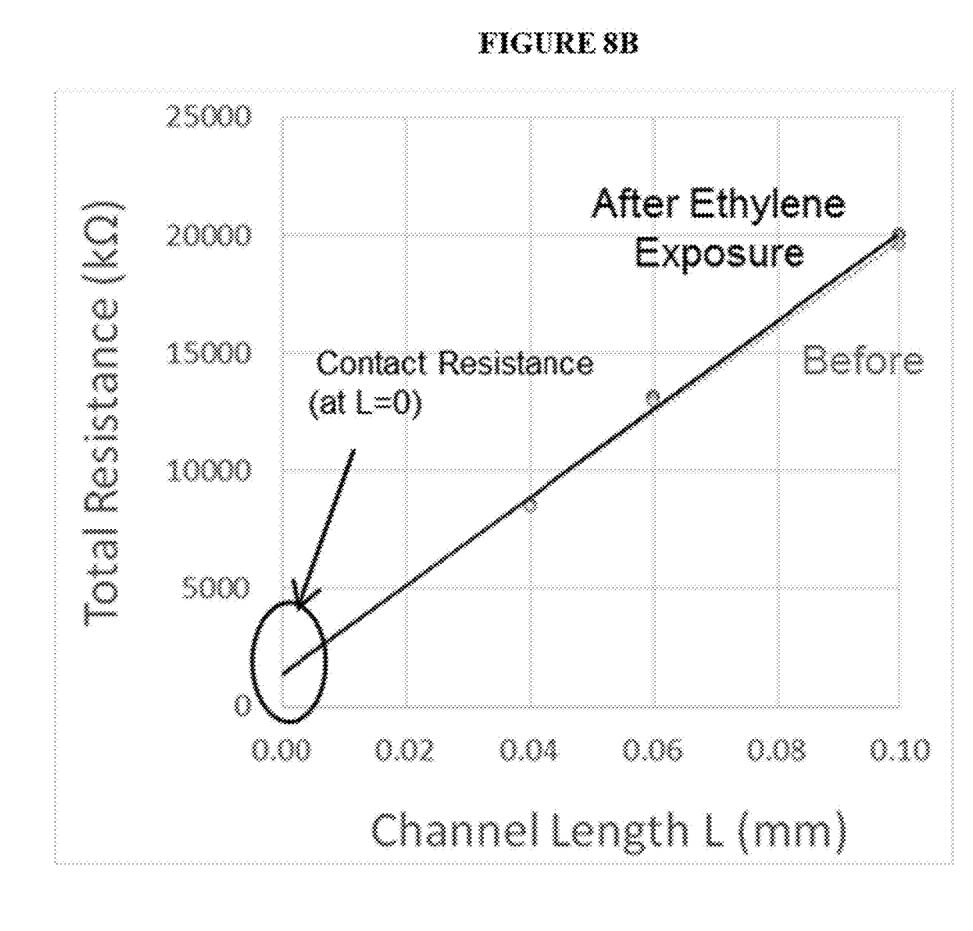
FIG. 8B is a graph of total resistance vs. channel length for a series of OTFT gas sensors having differing channel lengths in an inert (N2) environment and after exposure to ethylene.

With reference to FIG. 8B, there was little or no observable change in contact resistance before (dotted line) and after (solid line) exposure to ethylene.

Without wishing to be bound by any theory, it is believed that the dipole moment of 1-MCP causes it to bind to the electrodes, thereby increasing contact resistance at the electrode/semiconductor interface.

A series of OTFTs were formed as described above with channel lengths of 30, 40, 60 and 100 microns. The change in source-drain current of the devices was measured upon exposure to 250 ppm of 1-MCP.

Figure 9:
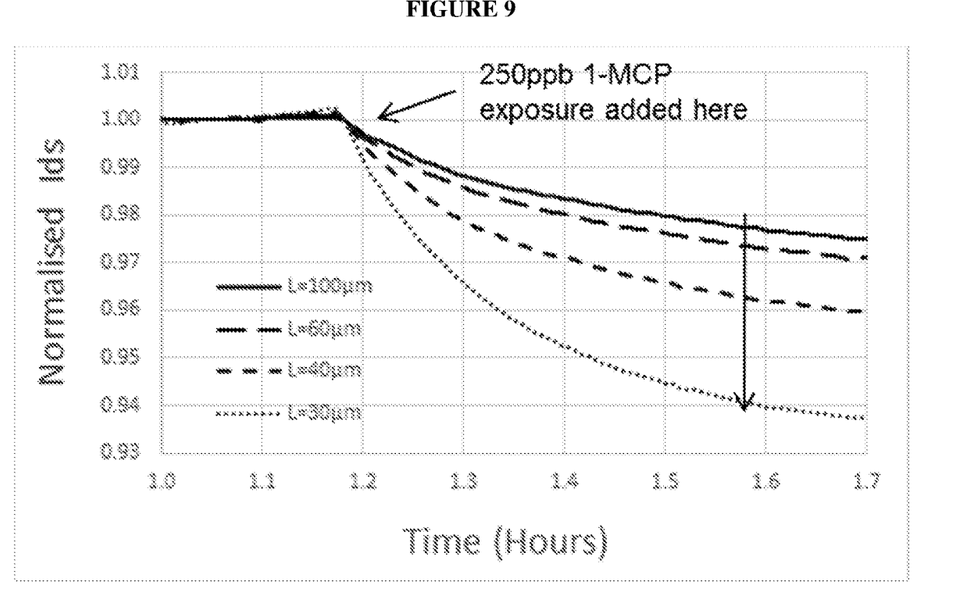
FIG. 9 is a graph of drain current vs. time for a series of OTFT gas sensors having differing channel lengths in an inert (N2) environment and after exposure to 1-MCP.
Figure 10:
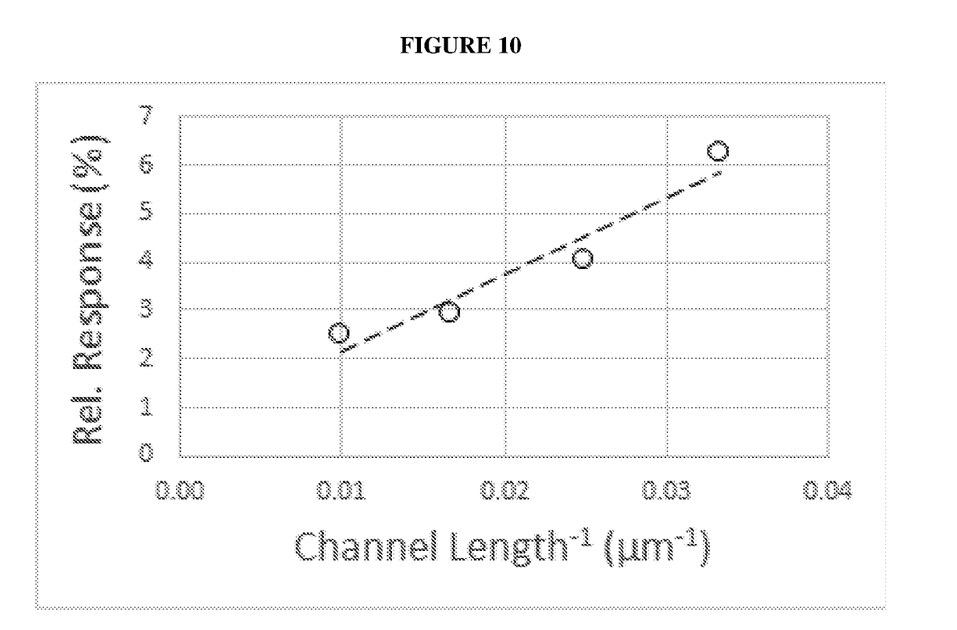
FIG. 10 is a graph of relative response vs. channel length for the OTFT gas sensors of FIG. 8.
Figure 11:
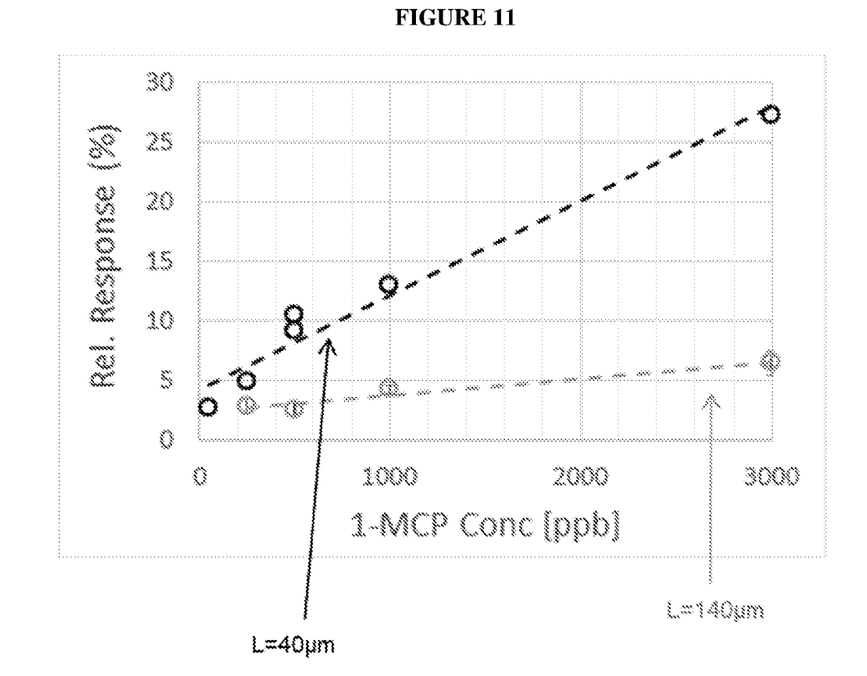
FIG. 11 is a graph of relative response vs. 1-MCP concentration for OTFT gas sensors having 40 micron and 140 micron channel lengths.

With reference to FIG. 9, a greater change in current is observed at shorter channel lengths. As shown in FIG. 10, this relative response is inversely proportional to the channel length. The same effect is observed for OTFTs having 40 micron and 140 micron channel lengths, as shown in FIG. 11.

Without wishing to be bound by any theory, this is attributed to a greater proportion of the total device resistance being due to the contact resistance at shorter channel lengths.

Enhancing Contact Resistance Proportion

The response to 1-MCP to OTFTs containing semiconductors of differing mobilities was measured.

Figure 12:
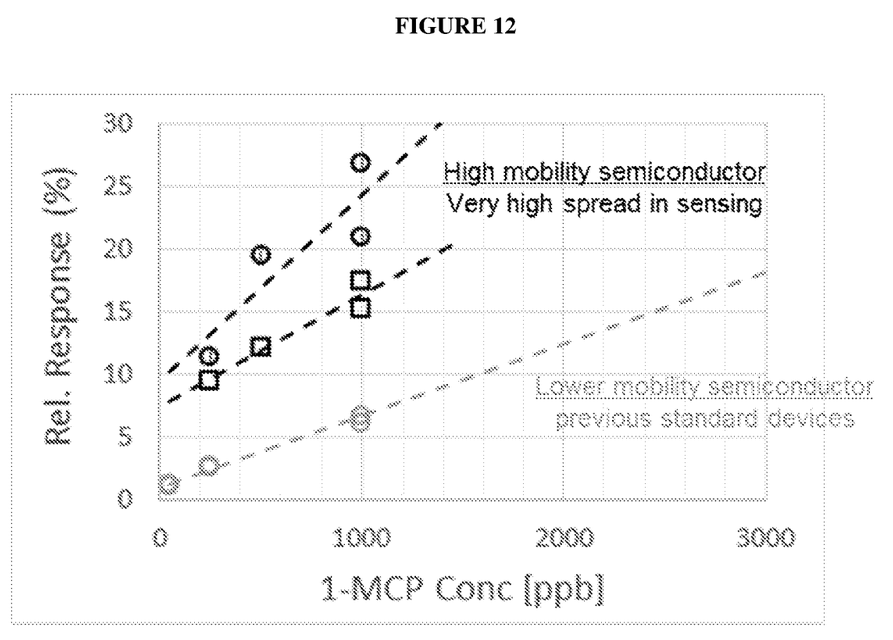
FIG. 12 is a graph of relative response vs. 1-MCP concentration for OTFT gas sensors having organic semiconductors of differing conductivities.

With reference to FIG. 12, a greater relative response was observed for higher mobility semiconductors. Without wishing to be bound by any theory, this is attributed to a greater proportion of the total device resistance being due to the contact resistance for higher mobility semiconductors.

What is claimed is:

1. A gas sensor system configured to determine a presence and/or a concentration of a plurality of gases in an environment, comprising:
    a first gas sensor;
    a second gas sensor, wherein the first gas sensor and the second gas sensor each comprise first and second electrodes and a semiconducting region comprising a semiconductor disposed between and in electrical contact with the first and second electrodes, and wherein a first distance between the first and second electrodes of the first gas sensor is greater than a second distance between the first and second electrodes of the second gas sensor;
    a resistance meter configured to measure a first resistance of the first gas sensor and a second resistance of the second gas sensor; and
    processing circuitry comprising instructions which when executed is configured to determine from the first and second resistances:
        a contact resistance component from the first and the second resistance; and
        a semiconducting region resistance component from the first and the second resistance;
    determining from the contact resistance component and the semiconducting region resistance component:
        a presence or a concentration of a first gas in the environment from the contact resistance component; and
        a presence or a concentration of a second gas in the environment from the semiconducting region resistance component,
    wherein the first gas sensor and the second gas sensor each comprise a thin film transistor and the first and second electrodes of the first and the second gas sensors comprise source and drain electrodes.

2. A gas sensor system according to claim 1, wherein the gas sensor system, further comprises:
    a third gas sensor comprising first and second electrodes and a semiconducting region comprising a semiconductor disposed between and in electrical contact with the first and second electrodes,
    wherein a third distance between the first and second electrodes of the third gas sensor is different from the first distance and the second distance.

3. A gas sensor system according to claim 1 wherein the first gas sensor and the second gas sensor each comprise a bottom gate thin film transistor (BG-TFT).

4. A gas sensor system according to claim 1, wherein the first gas sensor and the second gas sensor each comprise a chemiresistor.

5. A gas sensor system according to claim 1, wherein the semiconductor comprises an organic semiconductor.

6. A gas sensor system according to claim 1, wherein at least one of the first and the second gases comprises an alkene.

7. A gas sensor system according to claim 6, wherein the alkene comprises one of ethylene and 1-methylcyclopropene.

8. A gas sensor system comprising a plurality of gas sensors including at least one first gas sensing thin film transistor and at least one second gas sensing thin film transistor, each gas sensing thin film transistor comprising a gate electrode; a gate dielectric; source and drain electrodes; and a semiconducting region between and in electrical contact with the source and drain electrodes wherein a distance between the source and drain electrodes of the first gas sensing thin film transistor is greater than a distance between the source and drain electrodes of the second gas sensing thin film transistor.

* * * * *